(12) United States Patent
Leuchs et al.

(10) Patent No.: US 8,828,400 B2
(45) Date of Patent: Sep. 9, 2014

(54) ANTIBODY THAT BINDS TO H-1 PARVOVIRUS

(75) Inventors: Barbara Leuchs, Heidelberg (DE); Kathrin Kürschner, Heidelberg (DE); Andrea Kuck, Ittlingen (DE); Marcus Müller, Bad Rappenau (DE); Silvia Münstermann, Neckargemünd (DE); Jean Rommelaere, Heidelberg (DE)

(73) Assignee: Deutsches Krebsforschungszentrum Siftung des Öffentlichen Rechts, Heidelberg (DE)

( * ) Notice: Subject to any disclaimer, the term of this patent is extended or adjusted under 35 U.S.C. 154(b) by 0 days.

(21) Appl. No.: 13/513,502

(22) PCT Filed: Dec. 1, 2010

(86) PCT No.: PCT/EP2010/007301
§ 371 (c)(1),
(2), (4) Date: Aug. 13, 2012

(87) PCT Pub. No.: WO2011/069614
PCT Pub. Date: Jun. 16, 2011

(65) Prior Publication Data
US 2013/0028913 A1 Jan. 31, 2013

(30) Foreign Application Priority Data
Dec. 11, 2009 (EP) .................... 09015373

(51) Int. Cl.
*A61K 39/42* (2006.01)
*C07K 16/08* (2006.01)
*C12Q 1/70* (2006.01)
*G01N 33/569* (2006.01)

(52) U.S. Cl.
CPC ........ *C07K 16/081* (2013.01); *G01N 2333/015* (2013.01); *C07K 2316/96* (2013.01); *G01N 33/56983* (2013.01)
USPC .................. 424/159.1; 530/388.1; 530/388.3; 530/389.4; 530/391.1; 435/5; 435/339

(58) Field of Classification Search
CPC ......... A61K 39/42; C07K 16/081; C12Q 1/70
See application file for complete search history.

(56) References Cited

U.S. PATENT DOCUMENTS

2013/0028913 A1 * 1/2013 Leuchs et al. .............. 424/159.1

OTHER PUBLICATIONS

Kashmiri et al. (Methods. 2005; 36:25-34).*
Tamura et al. (Journal of Immunology. 2000; 164 (3):1432-1441).*
Greenspan et al (Nature Biotechnology. 17; 10:936-937 (1999).*
Paradiso et al. (Journal of Virology. 1981; 39 (3): 800-807).*
Casal et al. (Journal of Virology. 1995; 69 (11): 7274-7277).*
Langeveld et al. (Journal of Virology. 1993; 67 (2): 765-772).*
Raykov et al. (Oncology Reports. 2007; 17: 1493-1499).*

* cited by examiner

*Primary Examiner* — Shanon A Foley
(74) *Attorney, Agent, or Firm* — Leason Ellis LLP.

(57) ABSTRACT

Described is an antibody or an antigen binding fragment thereof specifically binding to a full or empty H-1 parvovirus capsid. Such an antibody is useful for various diagnostic and therapeutic methods, e.g., for the detection/therapy of an H-1 parvovirus infection during pregnancy since parvovirus affects about 1 in 400 pregnancies and may cause fetal loss or fetal hydrops.

12 Claims, 8 Drawing Sheets

|  | Capsids | | Negative-control |
|---|---|---|---|
|  | Denaturated | Native |  |
| BL-H1 |  |  |  |
| αVP |  |  |  |

ANTIBODY THAT BINDS TO H-1 PARVOVIRUS

CROSS-REFERENCE TO RELATED PATENT APPLICATIONS

This application is a U.S. National Phase Application under 35 U.S.C. §371 of International Patent Application No. PCT/EP2010/007301, filed Dec. 1, 2010, and claims the priority of European Patent Application No. 09015373.5, filed Dec. 11, 2009, all of which are incorporated by reference herein. The International Application was published in Germany on Jun. 11, 2011 as International Publication No. WO 2011/069614 under PCT Article 21(2).

The present invention relates to an antibody or an antigen binding fragment thereof specifically binding to a full or empty H-1 parvovirus capsid. Such an antibody is useful for various diagnostic and therapeutic methods, e.g., for the detection/therapy of an H-1 parvovirus infection.

Figure 1:
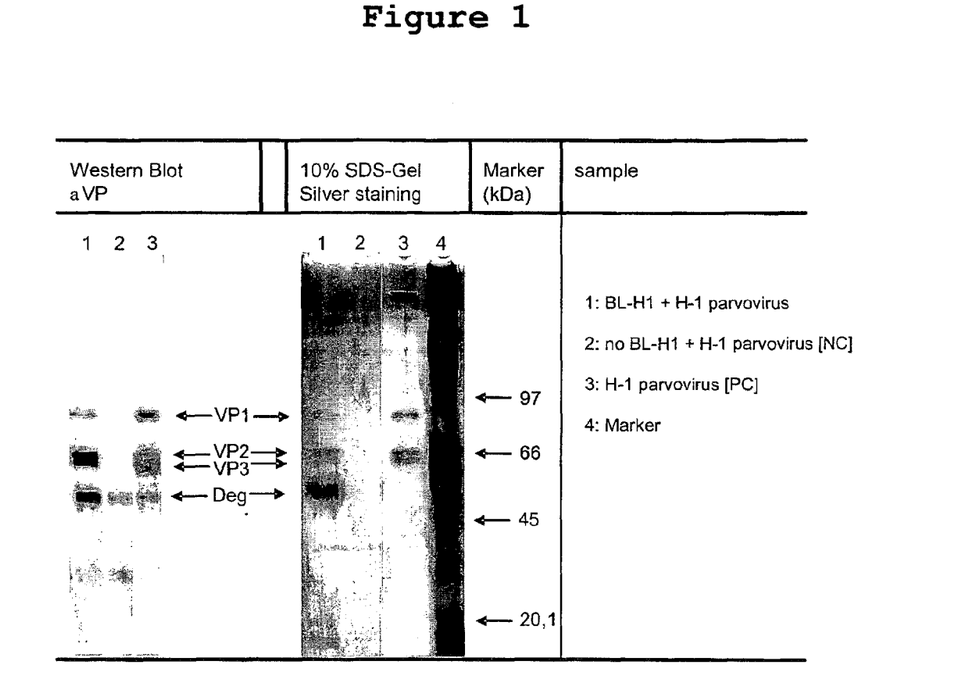
FIG. 1: Immune Precipitation of H-1 Parvovirus

Parvovirus designates a genus of the virus family Parvoviridae. The parvovirus genus comprises a number of small, icosaedric viruses that can replicate in the absence of a helper virus. Parvovirus contains a single-stranded DNA having a length of about 5.000 bp. At the 3' and 5' ends of the DNA there is one palindromic sequence each. The DNA codes for two capsid proteins, VP1 and VP2 [FIG. 1], as well as for two regulatory non-structure proteins, NS-1 and NS-2. The latter proteins are phosphorylated and show nuclear or both cytoplasmic and nuclear localization, respectively. V23, a third, smaller capsid protein, is derived from VP2 by proteolytic cleavage. The two capsid proteins VP1 and VP2 are encoded by overlapping open reading frames so that the VP2 encoding region is entirely comprised within the VP1 encoding region. In a natural infection capsid proteins are expressed in a VP1:VP2 ratio of 1:10 due to alternative splicing. Recently it has been shown that the region of the capsid proteins which is specific for VP1 (N-terminal region) contains motifs common to cellular phospholipase A and indeed exerts this activity in vitro. The calcium dependent, secreted $PLA_2$ to which parvovirus VP1 shares similarities, takes part in signaling pathways that involve cell lysis by permeabilizing membranes. On the other hand, NS1 has been shown to be regulated by members of the protein kinase C family, which in turn are subject to regulation through phospholipases.

The present invention relates to an antibody or an antigen binding fragment thereof specifically binding to a full or empty H-1 parvovirus capsid. Such an antibody is useful for various diagnostic and therapeutic methods, e.g., for the detection/therapy of an H-1 parvovirus infection.

Parvovirus designates a genus of the virus family Parvoviridae. The parvovirus genus comprises a number of small, icosaedric viruses that can replicate in the absence of a helper virus. Parvovirus contains a single-stranded DNA having a length of about 5.000 bp. At the 3' and 5' ends of the DNA there is one palindromic sequence each. The DNA codes for two capsid proteins, VP1 and VP2 [FIG. 1], as well as for two regulatory non-structure proteins, NS-1 and NS-2. The latter proteins are phosphorylated and show nuclear or both cytoplasmic and nuclear localization, respectively. VP3, a third, smaller capsid protein, is derived from VP2 by proteolytic cleavage. The two capsid proteins VP1 and VP2 are encoded by overlapping open reading frames so that the VP2 encoding region is entirely comprised within the VP1 encoding region. In a natural infection capsid proteins are expressed in a VP1:VP2 ratio of 1:10 due to alternative splicing. Recently it has been shown that the region of the capsid proteins which is specific for VP1 (N-terminal region) contains motifs common to cellular phospholipase A and indeed exerts this activity in vitro. The calcium dependent, secreted $PLA_2$ to which parvovirus VP1 shares similarities, takes part in signaling pathways that involve cell lysis by permeabilizing membranes. On the other hand, NS1 has been shown to be regulated by members of the protein kinase C family, which in turn are subject to regulation through phospholipases.

Parvoviruses are usually well-tolerated by populations of their natural host, in which they persist without apparent pathological signs. This is due to both the protection of foetuses and neonates by maternal immunity, and the striking restriction of parvovirus replication to a narrow range of target proliferating tissues in adult animals. This host tolerance concerns especially rodent parvoviruses, for example the minute virus of mice (MVM) and H-1 virus in their respective natural hosts, namely mice and rats.

In addition, humans can be infected with parvovirus, e.g., H-1 parvovirus. In fact, parvovirus is a common infection, usually presenting as erythema infectiosum in children. It is usually mild and self-limiting in healthy people. However, parvovirus can also cause reactive arthritis in adults, and severe anaemia in those with haematological conditions or immunocompromise. Moreover, parvovirus affects about 1 in 400 pregnancies and may cause fetal loss or fetal hydrops. Thus, identification of parvovirus infection, in particular in a pregnant woman is important for monitoring and possible treatment. Unfortunately, current methods for the diagnosis/therapy of a parvovirus infection need improvement, e.g., until now a specific antibody against assembled H-1 parvovirus is not available.

Thus, the technical problem underlying the present invention is to provide an improved means for diagnosis and treatment of a parvovirus infection or a disease associated therewith.

The solution to said technical problem is achieved by providing the embodiments characterized in the claims. After immunization of Balb/c mice with H-1 parvovirus antibody producing B cells could be isolated from spleen and fused with Ag8 myeloma cells by the inventors. After three rounds of selection using selection pressure the hybridoma cell line BL-H1 could be isolated which produces a monoclonal antibody directed against H-1 parvovirus.

Thus, the present invention relates to an antibody or an antigen binding fragment thereof specifically binding to a full or empty H-1 parvovirus capsid.

As used herein, the term "antibody" refers to an intact antibody, or a binding fragment thereof that competes with the intact antibody for specific binding. (Antigen) binding fragments are produced by recombinant DNA techniques, or by enzymatic or chemical cleavage of intact antibodies. Binding fragments include Fab, Fab', $F(ab')_2$, Fv, and single-chain antibodies as well as "diabodies". An antibody other than a "bispecific" or "bifunctional" antibody is understood to have each of its binding sites identical.

The term "capsid" as used herein is the protective coat of protein surrounding the viral nucleic acid which is formed from different or identical protein subunits called capsomers. The capsid is made from proteins encoded by the viral genome and its shape serves as the basis for morphological distinction. Virally coded protein subunits will self-assemble to form a capsid, generally requiring the presence of the virus genome. The parvovirus capsid consists of the proteins VP1, VP2 and VP3 as part of maturation of full particles.

As used herein, the term "full capsid" refers to a parvovirus capsid containing the viral nucleic acid, preferably a viable virus. The term "empty capsid" refers to a capsid without embedded nucleic acid.

In a preferred embodiment, the antibody of the present invention is an antibody (or an antigen binding fragment thereof) binding to a native H-1 parvovirus capsid but not to a denatured capsid, e.g., a capsid denatured by use of a detergent or heat.

In a more preferred embodiment, the antibody of the present invention (or an antigen binding fragment thereof) is a neutralizing antibody. As used herein, the term "neutralizing antibody" means an antibody that reduces or abolishes the biological activity of the parvovirus, e.g., replication and/or infectivity.

In an even more preferred embodiment, the antibody of the present invention is a monoclonal antibody. Monoclonal antibodies which specifically bind to H-1 parvovirus can be prepared using any technique which provides for the production of antibody molecules by continuous cell lines in culture. These techniques include the hybridoma technique, the human B cell hybridoma technique, and the EBV hybridoma technique (Kohler et al., Nature 256 (1985), 495-7). An entire capsid, VP1, VP2, VP3 or fragments thereof can be used to immunize a mammal, such as a mouse, rat, rabbit, guinea pig, monkey, or human, to produce polyclonal antibodies. If desired, the immunogen can be conjugated to a carrier protein, such as bovine serum albumin, thyroglobulin, and keyhole limpet hemocyanin. Depending on the host species, various adjuvants can be used to increase the immunological response. Such adjuvants include Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Techniques described for the production of single chain antibodies can be adapted using methods known in the art to produce single chain antibodies which specifically bind to the H-1 parvovirus capsid. Antibodies with related specificity, but of distinct idiotypic composition, can be generated by chain shuffling from random combinatorial immunoglobulin libraries [Burton, PNAS USA 88 (1991), 11120-3). Single-chain antibodies also can be constructed using a DNA amplification method, such as PCR, using hybridoma cDNA as a template [Thirion et al., Eur. J. Cancer Prev. 5 (1996), 507-11). Single-chain antibodies can be mono- or bispecific, and can be bivalent or tetravalent. Construction of tetravalent, bispecific single-chain antibodies is taught, for example, in Coloma & Morrison, Nat. Biotechnol. 15 (1997), 159-63). Construction of bivalent, bispecific single-chain antibodies is taught in Mallender & Voss, J. Biol. Chem. X no9 (1994), 199-206).

In the most preferred embodiment, the monoclonal antibody of the present invention is produced by the hybridoma cell line BL-H1 which has been deposited, in accordance with the Budapest Treaty in the DSMZ under the number DSM ACC3030 on Nov. 25, 2009.

The present invention also provides a monoclonal antibody or antigen binding fragment thereof, which binds to the same epitope as the antibody which is produced by the hybridoma cell line BL-H1 which has been deposited, in accordance with the Budapest Treaty in the DSMZ under the number DSM ACC3030 on Nov. 25, 2009.

As used herein, the term "epitope" includes any protein determinant capable of specific binding to an antibody. Epitopic determinants usually consist of chemically active surface groupings of molecules such as amino acids or sugar side chains and usually have specific three dimensional structural characteristics, as well as specific charge characteristics.

An antibody of the invention is said to specifically bind an antigen when the dissociation constant is ≤1 µM, preferably ≤µM 100 nM and most preferably, ≤10 nM. Typically, at least 6, 8, 10, or 12 contiguous amino acids are required to form an epitope. However, epitopes which involve non-contiguous amino acids may require more, e.g., at least 15, 25, or 50 amino acids.

The present invention also provides a monoclonal antibody or antigen binding fragment thereof, which competes for binding to a full or empty H-1 parvovirus capsid with an antibody of the invention as characterized above.

Preferably, the antibody or antigen binding fragment thereof carries a detectable label. The antibody/fragment can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

The present invention also relates to cell lines, i.e., cell lines that produce an antibody or an antigen binding fragment thereof according to the invention. Preferably, this cell line is a mammalian cell line. Mammalian cell lines available as hosts for expression are well known in the art and include any immortalized cell lines available from the DSMZ or American Type Culture Collection (ATCC), including CHO cells, NSO cells, HeLa cells, BHK cells, COS cells, Hep cells, and a number of other cell lines. Non-mammalian cells including bacterial, yeast, insect, and plants can also be used to express recombinant antibodies. The expression methods are selected by determining which system generates the highest expression levels and produces antibodies with the desired binding properties.

Antibodies produced by such cell line can be purified by methods well known in the art. For example, antibodies can be affinity purified by passage over a column to which a parvovirus capsid, or parvovirus envelope protein(s) are bound. The bound antibodies can then be eluted from the column using a buffer with a high salt concentration.

The most preferred cell line is the hybridoma cell line BL-H1 which was deposited, in accordance with the Budapest Treaty in the DSMZ under the number ACC3030 on Nov. 25, 2009.

The present invention also provides a nucleic acid which encodes a monoclonal antibody or an antigen binding fragment thereof according to the present invention. A nucleic acid encoding an antibody of the invention, e.g., a single-chain antibody, can be constructed using manual or automated nucleotide synthesis, cloned into an expression construct using standard recombinant DNA methods, and introduced into a cell to express the coding sequence. Alternatively, antibodies can be produced directly using, for example, filamentous phage technology (Verhaar et al., Int. J. Cancer 61 (1995), 497-501).

The present invention also provides a diagnostic composition comprising an antibody or antigen binding fragment thereof according to the invention. Such composition might be useful for the diagnosis of a parvovirus infection. In addition, such composition can be used for (a) quantitation of a H-1 parvovirus for H-1 parvovirus preparations and also in infected animals and patients (Viremia, Pharmacokinetic), e.g., via ELISA;

(b) detection of the H-1 parvovirus assembly and trafficking in cells.

(c) detection of contamination of H-1 parvovirus in laboratory animals in particular in rats.

For diagnosis, an antibody which specifically binds to a full or empty H-1 parvovirus capsid can be used in immunochemical assays, such as Western blots, ELISAs, radioimmunoassays, immunohistochemical assays, immunoprecipitations, or other immunochemical assays known in the art. Numerous protocols for competitive binding or immunoradiometric assays are well known in the art. Such immunoassays typically involve the measurement of complex formation between the immunogen and an antibody which specifically binds to the immunogen.

Diagnosis is not limited to a particular immunoassay procedure, and therefore is intended to include both homogeneous and heterogeneous procedures. Exemplary immunoassays which can be conducted include fluorescence polarisation immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

The present invention also provides a pharmaceutical composition comprising an antibody or antigen binding fragment thereof according to the invention and a pharmaceutically acceptable carrier. The antibody or antigen binding fragment thereof can be used, e.g., in a method for the treatment of a H-1 parvovirus infection or a disease associated therewith, using the capability of the antibody to neutralize the virus (antidot).

For therapy, the antibodies or antigen binding fragments thereof are present in an effective dose and combined with a pharmaceutically acceptable carrier. "Pharmaceutically acceptable" is meant to encompass any carrier, which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods.

The antibodies or antigen binding fragments thereof according to the invention can be administered to the subject at an effective dose. An "effective dose" refers to amounts of the antibodies or antigen binding fragments thereof that are sufficient to affect the course and the severity of the infection/disease, leading to the reduction or remission of such pathology. An "effective dose" useful for treating and/or preventing these infections, diseases, or disorders may be determined using methods known to one skilled in the art (see for example, Fingl et al., The Pharmocological Basis of Therapeutics, Goodman and Gilman, eds. Macmillan Publishing Co., New York, pp. 1-46 ((1975)).

Finally, the present invention also provides a kit useful for diagnosis or therapy of an H-1 parvovirus infection or a disease associated with such infection comprising an antibody or an antigen binding fragment thereof according to the invention. Preferably, the kit comprises a carrier means being compartmentalized to receive in close confinement therein one or more containers such as vials, tubes, and the like, each of the container means comprising one of the separate elements to be used in the assay. For example, one of the container means may comprise an antibody or antigen binding fragment thereof according to the invention which is, or can be, detectably labelled. The kit may also have containers containing buffer(s) and/or a container comprising a reporter-means (for example, a biotin-binding protein, such as avidin or streptavidin) bound to a reporter molecule (for example, an enzymatic or fluorescent label).

BRIEF DESCRIPTION OF THE DRAWINGS

Lane 1: H-1 parvovirus immune precipitated with BL-H1 monoclonal antibody; Lane 2: negative control meaning H-1 parvovirus without BL-H1 monoclonal antibody, so there is no immunoprecipitation; Lane 3: positive control: only H-1 parvovirus on SDS-Gel and Western blot without immunoprecipitation procedure; Lane 4: protein marker PBS: phosphate buffered saline; mAb BL-H1; aVP: polyclonal antibody recognizing denaturated H-1 parvovirus viral proteins.

Western Dot Blot is generated with native and denaturated H-1 parvovirus. BL-H1: monoclonal antibody against H-1 Parvovirus; aVP: polyclonal antibody recognizing denaturated viral proteins (with sodium dodecylsulfate polyacrylamide and Dithiotreitol); native: H-1 parvovirus untreated; negative control: without H-1 parvovirus.

In order to determine whether the monoclonal antibody BL-H1 reacts with capsids, mono-/oligomeric capsid proteins or denaturated capsid proteins, cell extract is prepared from 293T HEK cells, 24 h post transfection with pUC 19ΔHindIII cell extract is fractionated on linear sucrose gradient.

BL-H1: monoclonal antibody against H-1 Parvovirus; aVP: polyclonal antibody recognizing denaturated H-1 parvovirus viral proteins; plasmid pUC19ΔHindIII contains complete H-1 parvovirus genome; Vg: viral genome containing particles analysed by real time PCR; IU: infection units; HA: Hemagglutination of full or empty H-1 parvovirus.

After purification the BL-H1 antibody is stored at room temperature, 4° C. and −20° C., respectively. Activity is tested 21 days after by IF (immune fluorescence) on infected NB-324K cells. The positive control is a polyclonal antibody C8B10. The analysis is done via microscope Axioskop 2 plus and camera AxioCamMRc (magnification: 40×).

H-1 parvovirus neutralization is shown with MTT Assay measured at 550 nm (Abs 550 nm) with MOI of 1 either with wild type and recombinant H-1 parvovirus. B1-H1 concentrations from 0 ng to 5000 ng were tested, corresponding to 3E5 to 3E7 H-1 Parvovirus/μg BL-H1

H-1 parvovirus neutralization is shown by Plaque Assay on NB-324K cells with MOI of 1 and 10. Either 3E4 or 1E5 H-1 parvovirus were neutralised with 1 μg BL-H1.

NC=negative control; PC=positive control.

Recombinant H-1 parvovirus containing green fluorescence protein (GFP) with MOI of 1 and 10 are neutralized with B1-H1 concentration from 0 ng to 5000 ng are infected NB-324K cells. GFP is analysed with 40× magnification.

No infection inhibition effect with BL-H1 on NB-324K cells is seen by B1-H1 pre-incubation overnight (o/n) and infection followed by H-1 parvovirus.

H-1 parvovirus capsids are measured at 450 nm in spectrophotometer to evaluate the standard curve. Three different concentration (0.75 µg/ml; 0.5 µg/ml and 0.1 µg/ml second antibody) are used still now.

The following examples illustrate the invention.

EXAMPLE 1

General Methods (A) Immunization of Balb/c Mice With H-1 Parvovirus

Mice were immunized according to the following schedule:

(1) One Week Before Injection

After anesthesia 15 µl blood were taken through retro orbital puncturing (negative control).

(2) Immunization

Anesthesia: intraperitoneal [i.p.] injection of 100 µl 0.2% Xylazinhydrochlorid (Rompun, Bayer) in PBS and each 10 µg Ketaminhydrochloride (Ketavalt, Parke-Davis) each 10 g bodyweight in PBS.

(3) 1. Injection of H-1 Parvovirus

100 µl virus in 40% Visipaque-Ringer solution (=$7 \times 10^{10}$ viral genome containing particles [Vg]=$1.2 \times 10^8$ Plaque Forming Units [PFU])

+50 µl PBS

+150 µl incomplete Adjuvant

Mixing and injection s.c. on 4 different positions each 60 µl.

(4) 2. Injection of H-1 Parvovirus, 1 Month After First Injection

Procedure like 1. injection (5) 3. Injection of H-1 Parvovirus, 2 Month After First Injection Boost: 1 week before taking out the spleen 100 µl Virus ($7 \times 10^{10}$ Vg=$1.2 \times 10^8$ PFU)

+200 µl PBS i.p.

(B) Generation of Hybridomas

Hybridomas were generated according to the following schedule:

Media:

Working Medium: RPMI 1640 (Gibco No. R8758)

Hybridoma Medium: 500 ml RPMI 1640 (Gibco No. R8758)

+5 ml L-glutamine 200 mM (Gibco)

+5 ml Pen/Strep (Penicillin 10000 U/ml; Streptomycin 10 mg/ml (Gibco)

+10 ml Hepes 1M pH 7.2 (Sigma)

+50 ml FCS (fusion tested, 30 min heat inactivated 56° C.)

Selection medium: Hybridoma Medium+10 ml HAT concentrate 50× (Gibco)

BM Condi-Med (for selection) 10%

Fusion Reagent:

PEG 1500 (Roche No: 783641)

Cells:

Ag8/X63 (B-cell tumor cells)

Cells are thawed at least one week before fusion, cultivate in hybridoma medium, and splitted 1 day before fusion. Cells should be in the proliferating phase.

Fusion:

Preparation: 1-2 Days Before Fusion 1 day before fusion: split Ag8 cells (total 18; should be in proliferating phase).

Day of Fusion:

Warm up all media and solution up to 37° C.

Preparation of Ag8 Cells:

Pool the Ag8 cells, centrifuge 7 min 264×g, put them in 30-40 ml working medium and count the cells (~$1-2 \times 10^8$ cells).

Spleen Preparation:

After anesthesia kill the mouse, put it into ethanol 70% to disinfect and pin mouse to a sterile base, take the spleen with sterile tweezers and scissors and put it into working medium in a dish, puncture the heart to get the blood and collect it in a 1.5 ml tube. Look after lymph nodes.

Spleen Cells:

Cut the spleen several times with the scissors, break up the spleen with the sterile object slides (grind), take the spleen bag and rinse it with working medium, discard the spleen bag, homogenize the spleen cells with Pasteur pipette, collect the cell suspension in a 50 ml tube, let tissue of bag set and take supernatant into a new 50 ml tube, centrifuge the cells, 264×g, 7 min, wash the cells once with working medium, centrifuge the cells, 264×g, 7 min, take the pellet in 2-5 ml working medium, and count the cells (should be $5 \times 10^7$ up to $3 \times 10^8$ cells).

Fusion of Spleen Cells With Ag8 Cells:

Mix spleen cells: Ag8=3:1 in a 50 ml tube, centrifuge the mixed cells, 264×g, 7 min, each cell pellet should be not more than $1 \times 10^8$ cells total, discard supernatant, break the pellet by gently tapping the bottom of the tube, add 1 ml PEG 1500 to the pellet using a 1 ml pipette over a period of 1 min continuous swinging. Continue swinging for further 2 min, add carefully 10 ml selection medium over a period of 3 min by continue swinging. Add further 10 ml of selection medium, centrifuge the mixed cells 120×g, 7 min, discard the supernatant, break the pellet by gently tapping the bottom of the tube, wash again (add further 10 ml selection medium, centrifuge the mixed cells, 120×g, 7 min, break the pellet by gently tapping the bottom of the tube), prepare 96 well plate with 100 µl selection medium (each well $2 \times 10^5$ cells/well (=$2 \times 10^6$/ml, $2 \times 10^7$/10 ml).

Ag8 control: seed 1E4 Cells/well in selection medium (around 24 wells, not more).

Blood:

After 30 min (Hemagglutination), centrifuge (5000×g, 10 min), take serum in fresh tube (positive control).

Observation:

After 2-7 days: control Ag8 cells in HAT selection medium (should be dead).

After 1 week: feed the fused cells, take 100 µl pro well, discard, feed 100 µl fresh HAT selection medium.

After 2 weeks: Screening should be started (Medium with BM CondiMed 10%), Immunfluorescence, Western dot blot.

Selection:

Positive screened wells should be selected.

1. selection: POS well should be plated: each 96 well plate 5 cells/well, 1 cell/well;

2. selection: POS well should be plated: each 96 well plate 5 cells/well, 1 cell/well;

3. selection: POS well should be plated: each 96 well plate 5 cells/well, 1 cell/well.

(C) Production of Monoclonal Antibody Against H-1 Wt Capsid

Material:

Greiner Bio-one T-flask with sterile filter, 75 cm² or 150 cm²; RPMI medium with 10% FCS, 1% L-glutamine (2.5 mM), 1% P/S, 20 mM HEPES; BL-H1-Hybridoma cells; pipettes (5, 10, 20 ml); tubes (15, 50 ml); 1 l bottle; water bath; and centrifuge.

Information:
generation time of BL-H1: ~27 h;
suspension cells;
medium exchange: centrifuge medium with cells: 300×g; 10 min;
harvest of B1-H1: centrifugation: 5000×g; 5 min;
BL-H1 cell growth is better with higher glucose concentration;
RPMI contains 2 g/l glucose, increase of 3 or 4 g/l could be an improvement of antibody production;
cell densities up to $2 \times 10^6$ cells/ml are possible.
Production:
75 cm² flask with 10 ml, in 150 cm² flask with 20 ml cell suspension;
Cultivation of BL-H1 cells in RPMI medium. Cell density at the beginning: $2 \times 10^5$ cells/ml is ideal;
$1 \times 10^5$ cells/ml is also possible, but the cell growth is slower at the beginning; $3 \times 10^5$ cells/ml also possible, but then the cells have to be split after 2 d or 3 d, otherwise the vitality is decreased;
split the cells after 3 d (optional 4 d);
15-20% conditioned medium with fresh medium increases the cell viability after medium exchange.
(D) Purification of Monoclonal Antibody BL-H1 With Affinity Chromatography
Material:
ÄKTA Prime apparatus, GE Healthcare Europe GmbH, Freiburg; 70% ethanol (in $H_2O$); 20% ethanol (in $H_2O$); 20 mM sodiumphosphate-buffer pH 7.0 (equilibration buffer=buffer A); 1M Tris-HCl pH 9.0 (neutralisation buffer); 50 ml tubes; polystyrene round bottom tubes; 0.1M citric acid pH 4.0 (elution buffer=buffer B); HiTrap Protein A HP 5 ml column.
All buffers should be filtered with bottle-top filters and should be out gassed with ultrasound for 10 min at room temperature with 100% (480 W).
Procedure:
Use of Äkta prime system: Rinse the system with 20% ethanol first. Put tube A and tube B in 20% ethanol and push "Run stored Method" and choose program 1. Afterwards put tubes with $H_2O$ and choose again program 1. Now fill each tube with equilibration buffer and connect all tubes. The column is stored in 20% ethanol and should directly rinsed with equilibration buffer. The limit of pressure is 0.3 MPa. The flow rate with 100% buffer A (=0% buffer B) for Protein A column is 5 ml/min. Alternative protein G: 1 ml/min (independent of the amount of serial columns).
The Chromatography should be run in the main menu through "Manual Run". For rinsing and loading the following conditions are used:
Set method base (ml)
Set concentration % B (0%)
Set gradient (off)
Set flow rate (A: 1 ml/min, B: 5 ml/min)
Set fraction base (ml)
Set fraction size (0)
Set pressure limit (0.3 MPa)
Set buffer valve position (Pos 1)
Set injection valve position (load)
Start run
The chromatography should be run with in the main menu through "Manual Run". The column should be rinsed with buffer as long as the UV baseline is permanent. Before loading the column, put in manual run "auto zero", this resets the UV-baseline zero. Load "antibody medium" through tube A. Therefore put tube A in "antibody medium", hold on with "break", otherwise air bubbles comes in the system. Afterwards press "continue". At the end press "break" and turn back the tube A, press continue for washing. Wash as long as the UV-baseline is almost zero. The flow through during loading and washing should be collected in extra bottle (in case that the column is overloaded: this could be seen through additional increasing of UV signal. So, the flow through could be used for second time.
Turn to 100% buffer B, all other parameters are still the same.
Set method base (ml)
Set concentration % B (100%)
Set Gradient (off)
Set Flow Rate (A: 1 ml/min, B: 5 ml/min)
Set Fraction Base (ml)
Set Fraction Size (0)
Set Pressure Limit (0.3 MPa)
Set Buffer Valve Position (Pos 1)
Set injection Valve Position (Load)
Start Run
As soon as buffer B reaches the column, the antibody starts to elute. The UV-signal increases strongly. Fractions could be collected through fraction collector tube. It is recommended to collect at least two fractions, because of different antibody concentrations.
Because of collecting the fractions manually, you could set in Manual Run "set event mark" to see beginning and ending. The eluted fractions should be directly brought to pH 1 with neutralisation buffer. The first fraction could still contain a little of buffer A, therefore it is not easy to know in advance the volume of neutralization buffer. It should be checked with pH paper very fast to avoid instability. Recommended value for 100% Puffer B:

| Chromatography | Fraction Elution [ml] | Neutralisation buffer [ml] |
|---|---|---|
| Protein G | 0.8 | ~0.025 |
| Protein A | 2 | ~0.25 |

After the peak is on baseline, switch to buffer A
Set method base (ml)
Set concentration % B (0%)
Set Gradient (off)
Set Flow Rate (A: 1 ml/min, B: 5 ml/min)
Set Fraction Base (ml)
Set Fraction Size (0)
Set Pressure Limit (0.3 MPa)
Set Buffer Valve Position (Pos 1)
Set injection Valve Position (Load)
Start Run
Storage of column and system should be in 20% ethanol. Rinse whole system [see protocol P-19-2 A).
(E) H1-Capsid-ELISA
Material:
Flexible plate, 96 well, U-bottom without lid, BD Falcon; Lid for microplates, Greiner BioOne; Casein from bovine milk, Sigma; PBS+0.05% Tween; PBS (in $H_2O$); for coating: BL-H1 Fraction E1, 2 mg/ml $IgG_{2A}$ BL-H1 (10 mg/ml total protein, $IgG_{2A}$+foreign protein) in 0.1M glycine buffer neutralised with Tris-HCl, stored at 4° C.; for detection: BL-H1-HRP in sodiumphosphate buffer, appr. 1 mg/mL, frozen at −20° C., 10 μL per tube; Standard: HV Pool green 1-2/1-3/3-3/4-2/4-3/5-2/6-2/7-2 $1.5 \times 10^{11}$ Vg/ml, $7.5 \times 10^{11}$ capsids/ml in 40% Visipaque, stored at 4° C.; Positive control: P #30/07β, $9.1 \times 10^{11}$ Vg/ml in 40% Visipaque (~$1 \times 10^{13}$ Capsids/mL estimated), stored at 4° C.; Optical Adhesive Cover (Fa. Applied Biosystems); TMB, super slow, liquid substrate system for ELISA, Sigma, stored at 4° C.; Stop solution: 1N $H_2SO_4$, stored at room temperature; Multiskan EX Microtiterplate Photometer, Thermo Scientific.

Buffers:

Wash Buffer: Add 0.05% Tween to PBS (see stock solution for Western (Dot) Blot).

Coating solution: Prepare directly before use. Dilute E1 to 2.5 µg/ml in PBS (in $H_2O$), means 1:800. For one plate 10 ml of dilution.

Blocking Buffer (BB): 2 mg/ml Casein in PBS+0.05% Tween. Always prepare fresh.

Heat 400 mL PBS+0.05% Tween to ~50° C. (for 40-50 sec in microwave), pour it into a beaker and add the needed amount of Casein. Stir with heating for 30 min, around 50° C. to 1 h until everything is dissolved. Cool down to 37° C. in water bath for use. 100 ml is enough for one plate.

Detection: Prepare directly before use. Dilute BL-H1-HRP (2.Ab) to 0.1 µg/ml in blocking buffer, means 1:10.000. For one plate 10 ml of dilution.

Standard: Dilute HV pool green to a standard between $2.5 \times 10^9$ and $3.91 \times 10^7$ capsids/well. For two standard rows: Prepare 600 µl of a $2.50 \times 10^9$ (douplex) capsids/well standard from the stock standard by 1:30 ($2.5 \times 10^{10}$ capsids/ml) dilution in blocking buffer. Add 300 µL blocking buffer to 6 1.5 ml tubes and label as 1.25E+09, 6.25E+08, 3.13E0+8, 1.56E+08, 7.81E+07, 3.91E+07 capsids/well. Perform serial dilutions by adding 300 µl of each standard to the next tube and vortexing between each transfer. PBS serves as Blank (blocking buffer also useable).

Positive control: Dilute 1:700 in BB, gives around $4.2 \times 10^9$ capsids/well resp. $2.9 \times 10^{12}$ capsids/well in original. Perform at least 4 wells with control per plate. As negative control for P#30/07β dilute 40% Visipaque 1:700 in BB.

Performance:

d0

In the afternoon: Coat flexible plate over night at 4° C. with 100 µl/well of coating solution. Close plate with lid for micro plates. Perform this carefully not to press the liquid out of the wells against the lid.

d1

Alternatively, the plate can be coated in the morning with incubation for 2 h at RT.

1. Prepare blocking buffer as described above. Remove coating solution from the plate by inverting and blotting on absorbent paper to remove any residual coating solution. Add 200 µl/well of blocking buffer, close plate with lid and incubate at 37° C. for 1 h.

2. During blocking the plate, prepare standard and positive control as described above. For sample dilutions estimate the capsids/ml via the Vg/ml titer. Make several dilutions around estimated value to cover a broader range. Prepare negative control with buffer of the sample matrix (pay attention to dilution of sample!).

3. Aspirate wells and wash 2 times with 200 µl/well wash buffer. After last wash, invert plate and blot on absorbent paper towel to remove any residual buffer.

4. From here all steps with plate under sterile hood. Add 100 µl of standard, positive control, resp. negative control or sample to each well. Close plate with lid. Incubate at 37° C. for 1 h.

5. Remove positive control, resp. negative control or sample with a pipette, changing the tips for different samples. Wash 3 times with 200 µl/well wash buffer. After last wash, dry surface of the plate with paper towel. Collect waste in a beaker.

6. Add 100 µl/well diluted BL-H1-HRP to each well. Close the plate with the lid and incubate at 37° C. for 1 h.

7. Remove detection antibody with a 12-channel pipette. Wash 4 times with 200 µl/well wash buffer. After last wash, dry surface of the plate with paper towel. Try to remove as much liquid as possible. Collect waste in a beaker (12-channel pipette can be used) under sterile hood.

8. Still under sterile hood: Add 100 µl/well TMB solution to each well and incubate for around 15 min at RT in the dark. Check after around 10 min whether intensity of reaction is fine.

9. Stop reaction by adding 100 µl/well of stop solution to each well. Seal plate with Optical Adhesive Cover.

10. Read absorbance at 450 nm within 30 min. to stop reaction. Use Multiskan EX Microtiterplate photometer. For optional correction of the results read the plate additionally at 550 nm and 595 nm.

Additional Advice:

Blocking should not be performed over a longer period of time than over night. Longer incubation leads to formation of aggregates etc. All dilutions of virus and antibody should be prepared directly before use. Wells should be rinsed carefully to avoid loss of bound antibody. In addition it is important to add TMB in equal time steps to each row. The same time steps should be used for to stop the reaction, to minimize variation between two rows. When removing the remaining liquid with a pipette touch the bottom of the well only lightly and do not scratch, to avoid loss of bound reactants. Incubation of the plate at 37° C. can cause border effects because polystyrene is a weak heat conductor. Therefore it is important to keep the blocking buffer during the performance of the assay on 37° C. This will minimize the border effects to a lower level. The labelled second antibody should not be frozen again after use. This would lead to a lower intensity of the signal. The blocking buffer containing the Casein can be stored at least for 4 weeks frozen at −20° C. The dilution procedure should be performed carefully, as mistakes here lead to incorrect results. Not to many dilutions one after the other should be performed and they should be made very exact.

EXAMPLE 2

Characterization of BL-H1 Monoclonal Antibody Against H-1 Capsid

To assess the capacity of BL-H1 antibody to immune precipitate H-1 parvovirus, antibody and parvovirus were incubated together overnight at 37° C. Immune complexes were precipitated by protein A sepharose and analysed by western blotting using an antibody against denaturated viral proteins. This shows that BL-H1 antibody recognizes assembled H-1 parvovirus capsid [FIG. 1].

Figure 2:
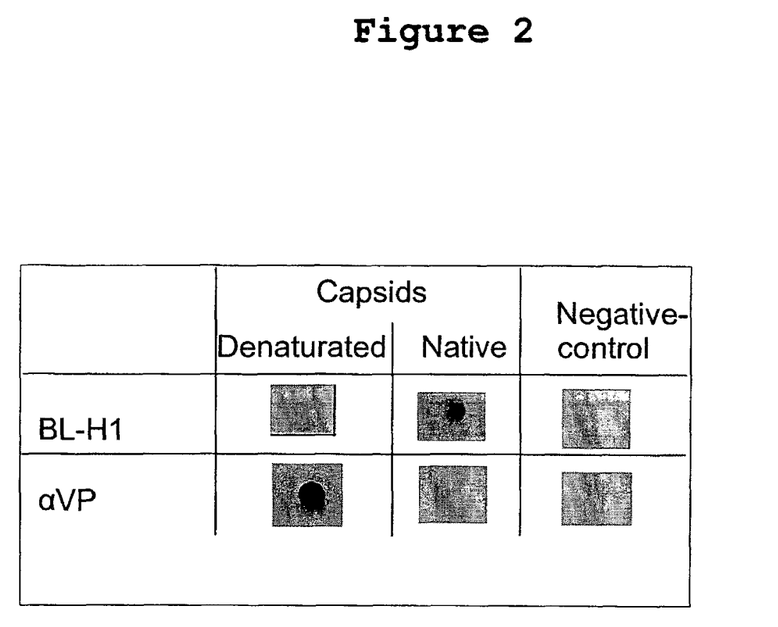
FIG. 2: Western Dot Blot

To characterize this identification either the native or dentaturated H-1 parvovirus was transferred to nitrocellulose membrane [FIG. 2]. BL-H1 antibody recognizes only native particles while polyclonal antibody recognizes dentaturated capsids.

Figure 3:
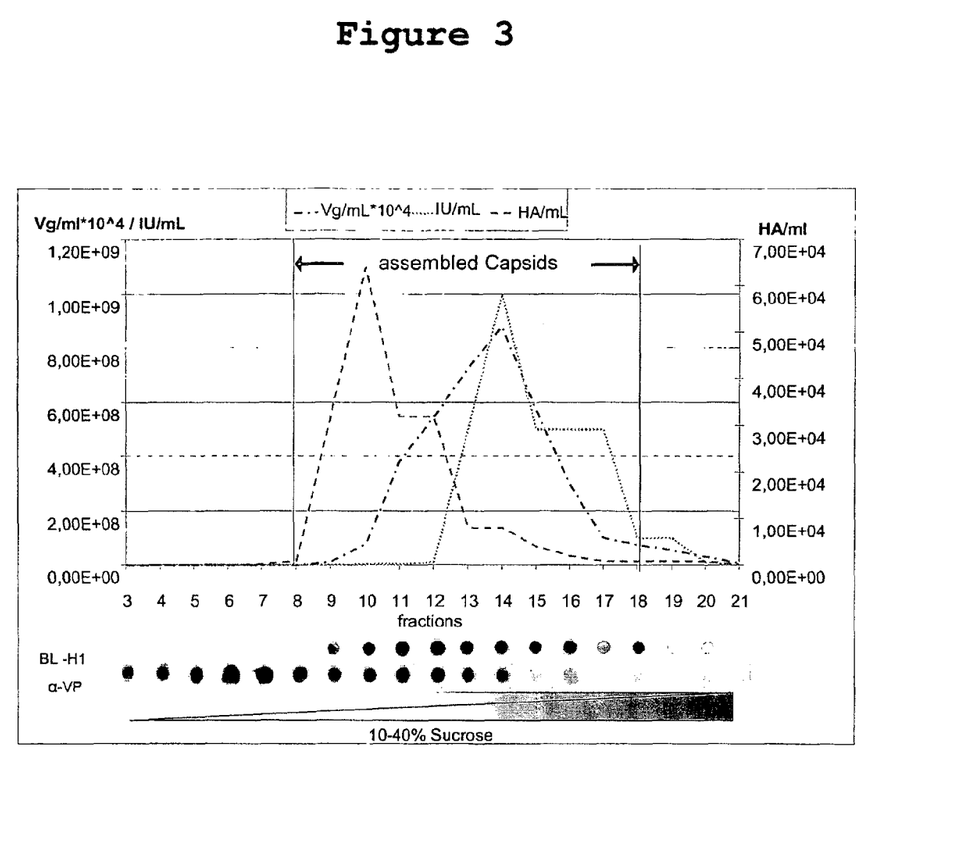
FIG. 3: Distribution of H-1 Wt and Detection with BL-H1 Monoclonal Antibody

In order to determine whether BL-H1 antibody reacts with capsids or also with native viral proteins, extracts of 293T cells transfected with capsid protein expression plasmids were prepared and fractionated on linear sucrose gradient [FIG. 3]. BL-H1 shows a peak between fractions 8-18 corresponding to empty and full H-1 parvovirus particles. The full or empty capsids are demonstrated via hemagglutination [fractions 8-17]. Full capsids are determined via viral genome containing particles [fractions 10-17] and active particles via infection units [fractions 12-18]. In contrast non-assembled viral proteins were detected in fractions 3-14 with an antibody against viral proteins. Finally, there is no reactivity of BL-H1 with non-denaturated as well as denaturated capsid proteins. BL-H1 recognizes specifically conformational epitopes present on assembled H-1 parvovirus capsids. All together this shows that BL-H1 recognizes structural epitopes displayed only by assembled particles.

Figure 4:
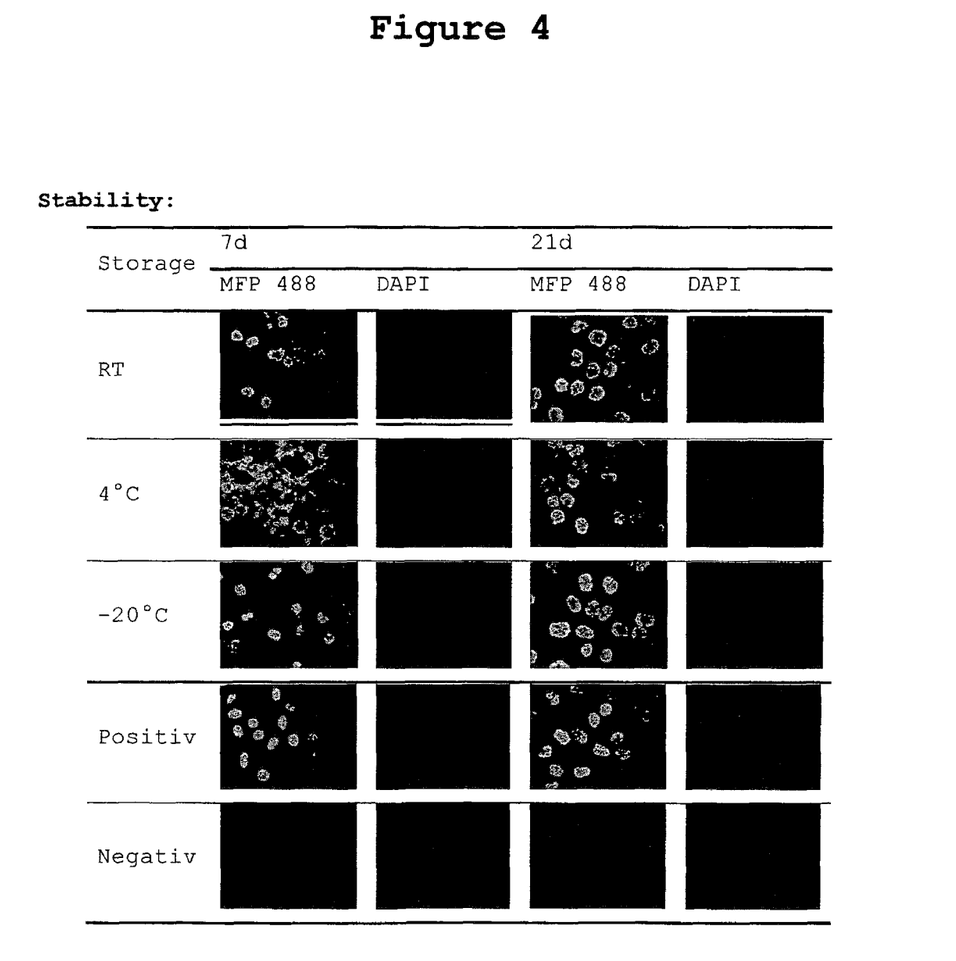
FIG. 4: Immunofluorescence Test of Mab BL-H1 (Stability of BL-H1 Activity 7 and 21 Days after Purification)

FIG. 4 shows the detection of H-1 production in infected NB-324K cells with BL-H1 by immune fluorescence. The BL-H1 antibody is stable at least for 3 weeks stored by room temperature, 4° C. and −20° C.

Figure 5:
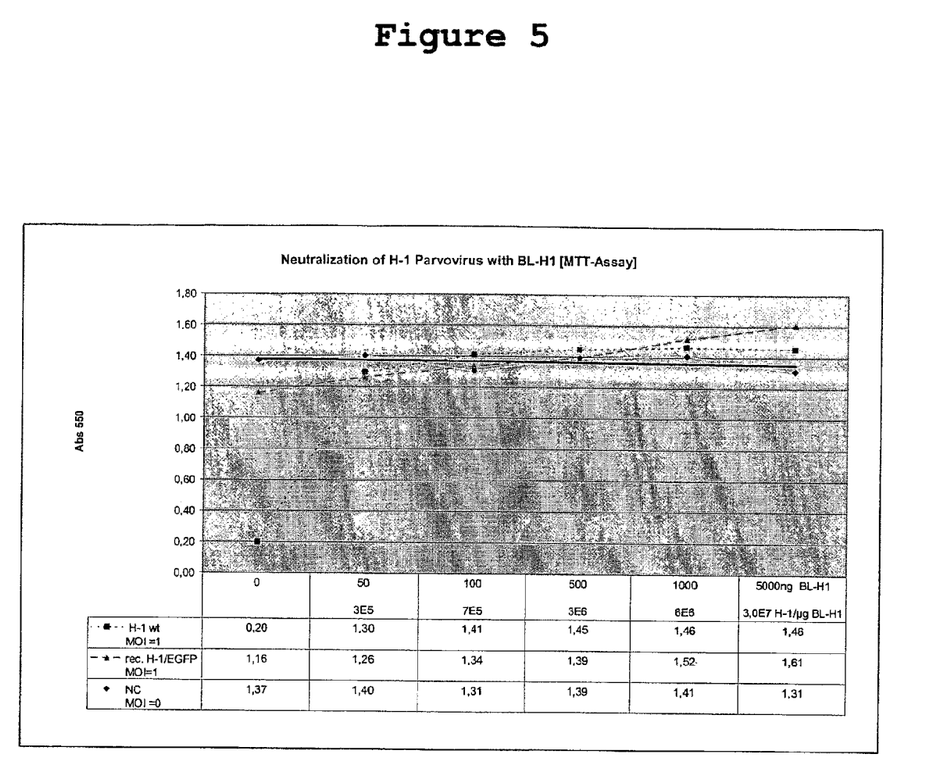
FIG. 5: Neutralisation of Infected NB-324 K Cells with H-1 Parvoviruses
Figure 6:
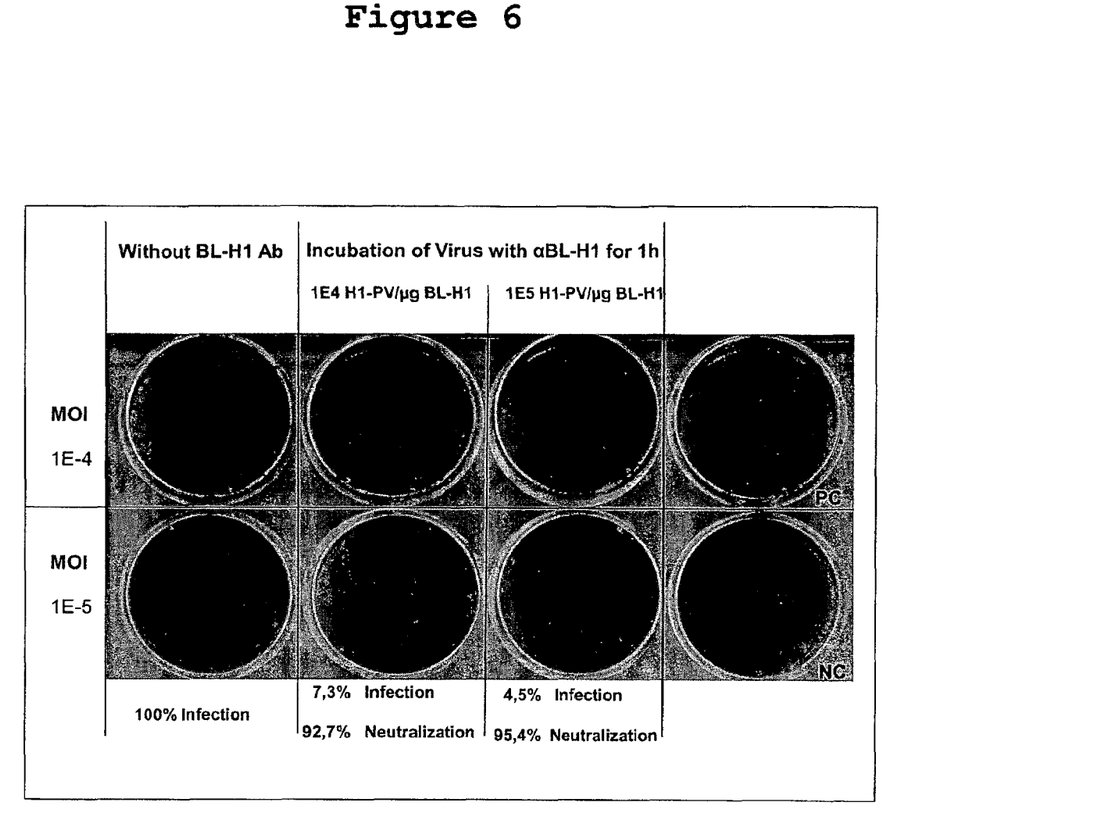
FIG. 6: Neutralisation of H-1 PV Wt with Mab BL-H1
Figure 7:
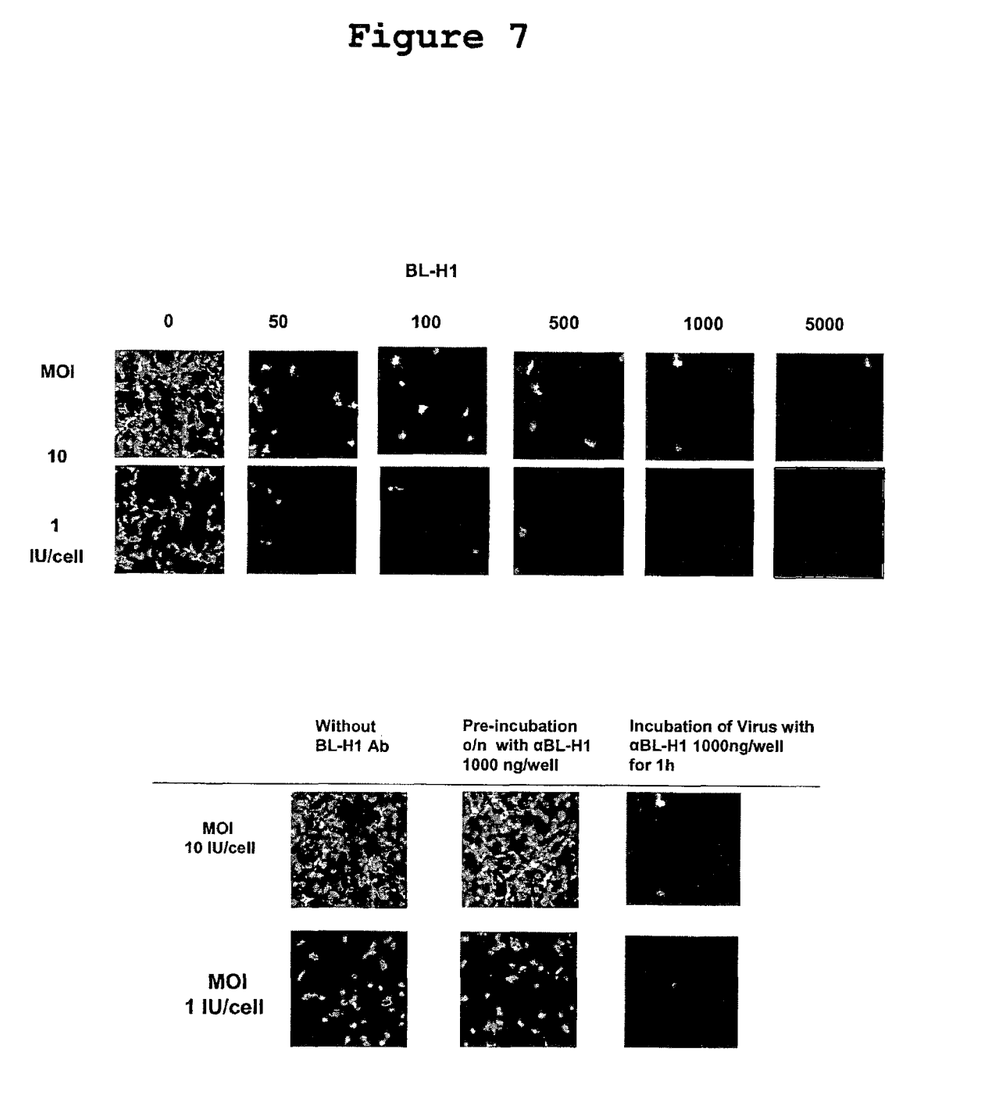
FIG. 7: Rec. H-1 EGFP (Green Fluorescence Protein)

In FIGS. 5,6 and 7 the ability of BL-H1 neutralization of H-1 parvovirus is demonstrated.

MTT-Assay was done to find out the right ratio between H-1 parvovirus and BL-H1 antibody. 1 μg BL-H1 is efficient to neutralize up to 1E5 H-1 parvovirus [FIG. 5].

95% neutralization could be achieved with 1 μg BL-H1 per 1E5 H-1 parvovirus determined by plaque assay [FIG. 6]. This neutralization capacity is also shown with recombinant H-1 parvovirus expressing green fluorescence protein [FIG. 7 upper panel]. To show that BL-H1 itself does not act indirectly by interacting with cellular receptors, NB-324K cells were pre-incubated with BL-H1 antibody overnight and afterwards infected with H-1 parvovirus [FIG. 7 lower panel].

EXAMPLE 3

H-1-Capsid ELISA

Figure 8:
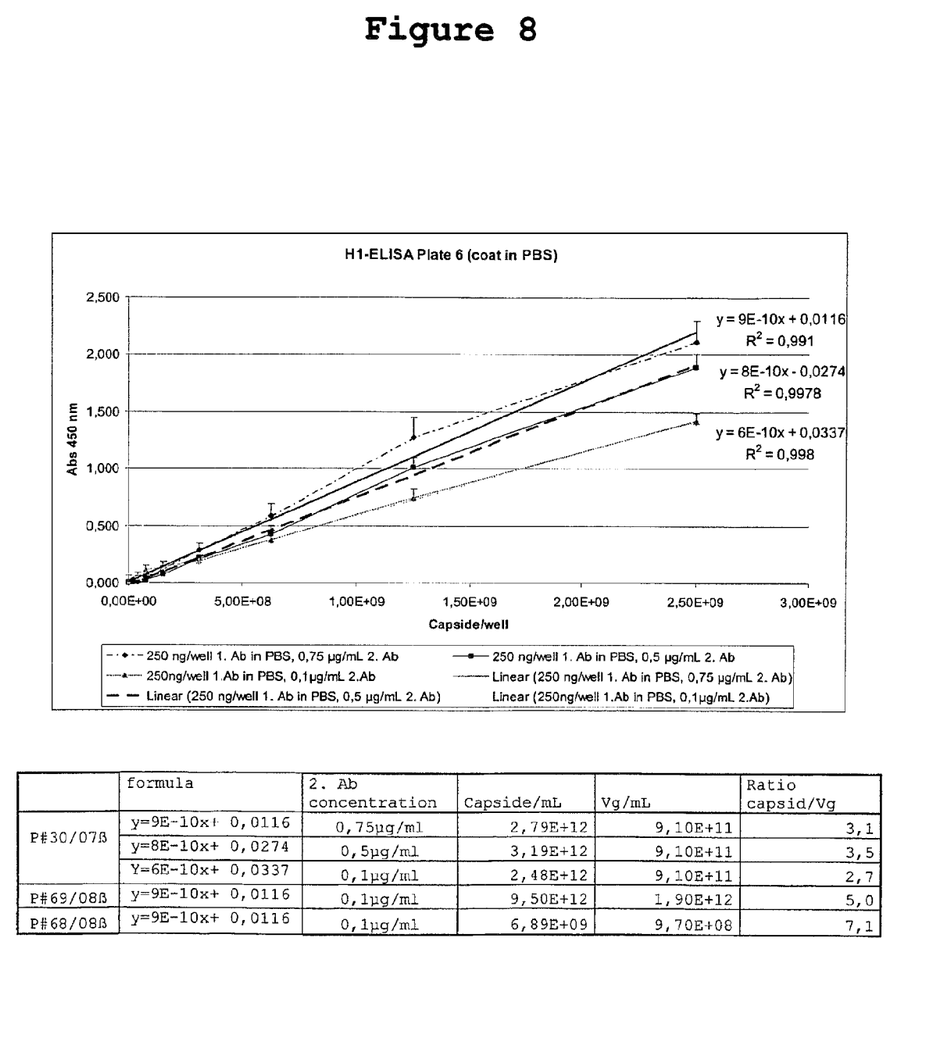
FIG. 8: ELISA Development for H-1 PV Detection

Quantification of H-1 parvovirus using BL-H1 with ELISA has been evaluated. First results show a ratio between capsids and viral genome-containing particles, of about 5 [FIG. 8, lower part]. Three concentrations of second antibody (0.1 μg/ml to 0.75 μg/ml) were used, showing no significant difference in recovery [FIG. 8, upper part].

The invention claimed is:

1. A monoclonal antibody or an antigen binding-fragment thereof specifically binding to a full or empty H-1 parvovirus capsid, wherein said monoclonal antibody or antigen binding-fragment competes for binding with the antibody produced by the hybridoma cell line BL-H1 having the accession number ACC3030.

2. The monoclonal antibody or an antigen binding fragment thereof according to claim 1 binding to a native H-1 parvovirus capsid but not to a denatured capsid.

3. The monoclonal antibody or an antigen binding fragment thereof according to claim 2, wherein the denatured capsid is denatured by a detergent or heat.

4. The monoclonal antibody or an antigen binding fragment thereof, which is a neutralizing antibody.

5. The monoclonal antibody according to claim 1, which is produced by the hybridoma cell line BL-H1 which has been deposited in the DSMZ under the number ACC3030.

6. The monoclonal antibody or antigen binding fragment thereof according to claim 1 carrying a detectable label.

7. A cell line that produces the monoclonal antibody or an antigen binding fragment thereof according to claim 1.

8. The cell line of claim 7, which is the hybridoma cell line BL-H1 which was deposited in the DSMZ under the number ACC3030.

9. A diagnostic composition comprising the monoclonal antibody or antigen binding fragment thereof according to claim 1.

10. A pharmaceutical composition comprising the monoclonal antibody or antigen binding fragment thereof according to claim 1, and a pharmaceutically acceptable carrier.

11. A kit useful for diagnosis or therapy of an H-1 parvovirus infection or a disease associated with such infection comprising the monoclonal antibody or an antigen binding fragment thereof according to claim 1.

12. The kit according to claim 11, further comprising at least one buffer.

* * * * *